United States Patent [19]

Doumaux, Jr. et al.

[11] Patent Number: 4,879,401
[45] Date of Patent: Nov. 7, 1989

[54] PROCESS FOR REMOVAL OF IMPURITIES IN ALKYL NITRITE FORMATION

[75] Inventors: Arthur R. Doumaux, Jr., Charleston; James R. Nelson, S. Charleston, both of W. Va.

[73] Assignee: Union Carbide Chemicals and Plastics Company Inc., Danbury, Conn.

[21] Appl. No.: 102,370

[22] Filed: Sep. 29, 1987

[51] Int. Cl.$^4$ .............................................. C07C 77/00
[52] U.S. Cl. ..................................................... 558/488
[58] Field of Search .......................................... 558/488

[56] References Cited

U.S. PATENT DOCUMENTS

| | | | |
|---|---|---|---|
| 2,166,698 | 7/1939 | Allen | 558/488 |
| 2,739,166 | 3/1956 | Treacy | 558/488 |
| 2,831,882 | 4/1958 | Spaeth | 558/488 |
| 4,353,843 | 10/1982 | Doumaux, Jr. et al. | 558/488 |
| 4,629,806 | 12/1986 | Cleveland et al. | 560/204 |

Primary Examiner—John F. Terapane
Assistant Examiner—Susan Wolffe
Attorney, Agent, or Firm—Morris N. Reinisch

[57] ABSTRACT

A process is provided for removing impurities from the gaseous product of an alkyl nitrite production zone by contacting a portion of it with lower alcohol and oxygen to convert substantially all of the nitric oxide in that portion of the gaseous product stream to alkyl nitrite, the oxygen being present in an amount such that the mole ratio of nitric oxide to oxygen is in the range of about 4:1 to about 2:1 and the lower alcohol being present in the reaction zone such that the mole ratio of nitric oxide to lower alcohol is about 1:1 or less. A recovery stream, comprising alkyl nitrite substantially free of nitric oxide, is withdrawn from the reaction zone and at least a portion of the alkyl produced in the reaction zone is removed. A least a portion of the balance of the recovery stream from which the alkyl nitrite has been removed is purged, thereby removing impurities from the process.

25 Claims, 1 Drawing Sheet

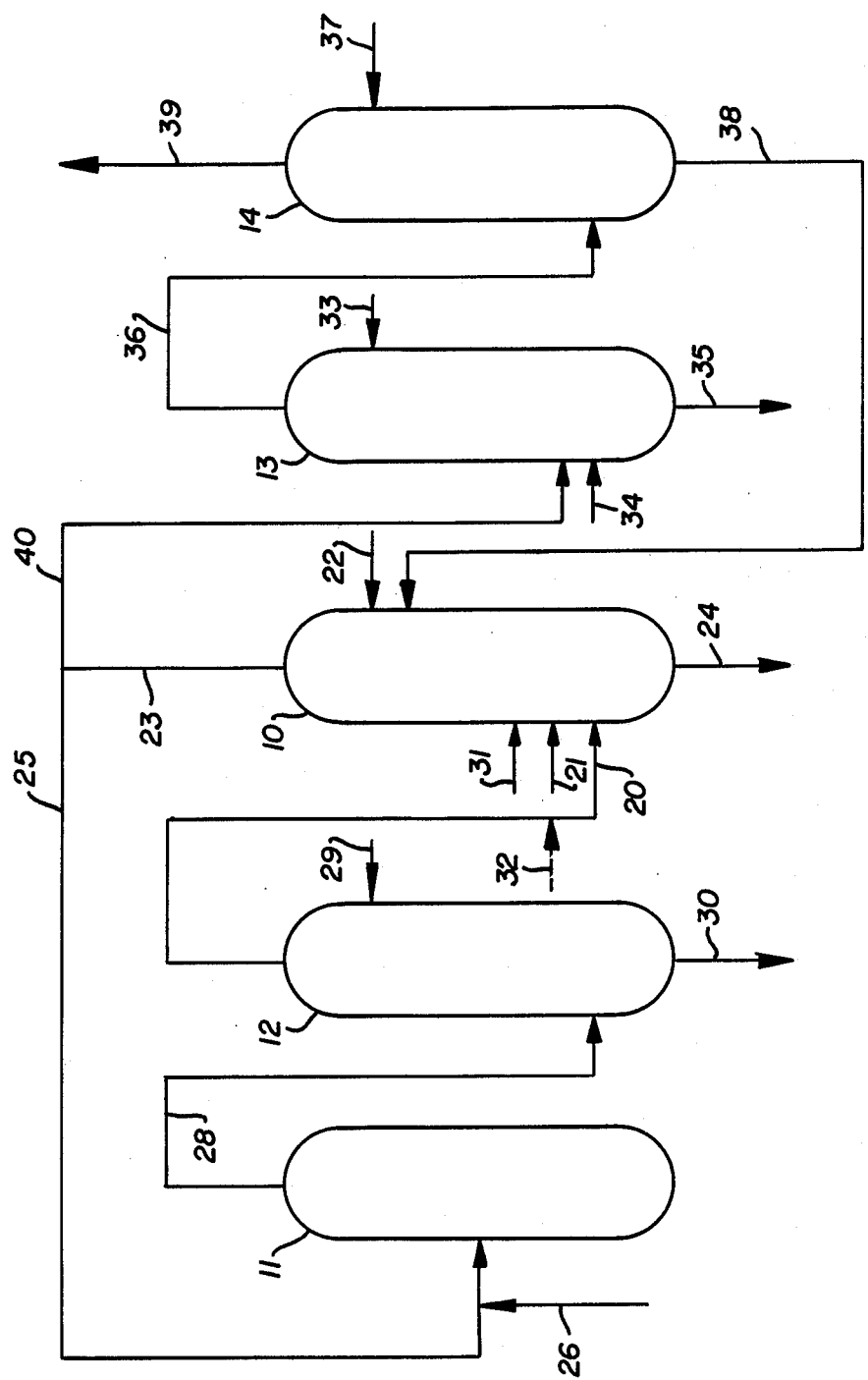

PROCESS FOR REMOVAL OF IMPURITIES IN ALKYL NITRITE FORMATION

BACKGROUND OF THE INVENTION

1. Field of the Invention

The subject invention is directed to a process for preparing alkyl nitrites, particularly methyl nitrite and ethyl nitrite. More particularly, the subject invention is directed to a process for removing impurities from an alkyl nitrite production zone gaseous product stream in an integated cycle wherein the production of alkyl nitrite and subsequent conversion of alkyl nitrite to dialkyl oxalate are coupled.

2. Description of Related Art

Alkyl nitrites, i.e., esters of nitrous acid, have been found useful in a variety of areas including additives to motor fuels, stabilizers for vinyl compounds such as spasmolytic agents, reagents for diazotization and reagents for chemical synthesis. Processes for preparing alkyl nitrites can be found, inter alia, in U.S. Pat. Nos. 4,229,591; 4,353,843 and 4,629,806 and in Japanese Application No. 53-8268. The process for forming alkyl nitrites (referred to herein as the nitrite process) may be understood more fully by reference to the following equations:

(1) $2NO + O_2 \rightarrow 2NO_2$
(2) $NO_2 + NO \rightleftarrows N_2O_3$
(3) $ROH + N_2O_3 \rightarrow RONO + HONO$
(4) $ROH + HONO \rightarrow RONO + H_2O$
(5) $N_2O_3 + H_2O \rightarrow 2HONO$
(6) $2NO_2 \rightleftarrows N_2O_4$
(7) $ROH + N_2O_4 \rightarrow RONO + HNO_3$
(8) $N_2O_4 + H_2O \rightarrow HONO + HNO_3$ wherein R represents a methyl or ethyl group.

The desired reaction sequence for the formation of alkyl nitrite occurs via Reactions (1)–(4). The sum of these reactions yields as the overall process reaction:

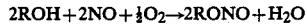

$$2ROH + 2NO + \tfrac{1}{2}O_2 \rightarrow 2RONO + H_2O \qquad I$$

Reaction (5) takes place because the water formed in Reaction (4) can react with dinitrogen trioxide ($N_2O_3$). Reaction (5) can be tolerated provided enough alcohol is supplied to react with substantially all of the nitrous acid formed in Reaction (5) according to Reaction (4) yielding alkyl nitrite and additional water.

Reactions (6) through (8) are undesired since they lead to the formation of nitric acid, a compound which subsequently must be separated from product alkyl nitrite. Further, these reactions consume nitric oxide in forming undesired nitric acid. In order to reduce production of dinitrogen tetroxide ($N_2O_4$), via Reaction (6), the gas phase concentration of $NO_2$ should be minimized relative to that of NO. In this way, $N_2O_3$ preferentially is formed instead of $N_2O_4$. A relatively high NO to $NO_2$ ratio can be maintained by initially supplying a molar excess of NO relative to $O_2$, as indicated by the stoichiometry of Reaction (I), i.e., greater than 4 moles NO per mole $O_2$. In other words, to enhance production of alkyl nitrites such as methyl nitrite or ethyl nitrite, it generally is preferable to provide NO in a molar excess, preferably in such an amount that substantially all $O_2$ is consumed.

Vapor state formation of alkyl nitrite (nitrite process) by the general procedure described above preferably is coupled and correlated with vapor state formation of dialkyl oxalate from alkyl nitrite and carbon monoxide (oxalate process) in an integrated production cycle so as to provide an overall vapor state process (nitrite-oxalate process) that is cyclic in operation, e.g., see U.S. Pat. No. 4,629,806. Such a process is advantageous with regard to limiting the formation of by-products, ease of operation and production efficiency. Vapor state formation of dialkyl oxalate is conducted by contacting carbon monoxide and alkyl nitrite in a carbonylation reaction zone in the presence of a solid catalyst. The main reaction is illustrated by the following equation:

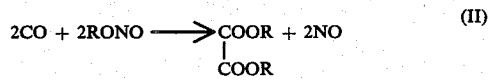

wherein R represents a methyl or ethyl group.

Preparation of dialkyl oxalates is of particular interest to the chemical industry because of the varied used of these compounds. These diesters may serve as starting materials for the preparation of alkylene glycols such as ethylene glycol, a valuable commercial chemical which finds application in deicing fluids, antifreeze, hydraulic fluids and in the manufacture of alkyd resins, solvents, and polyester fibers. These diesters also are useful as intermediates in preparing dyes, pharmaceuticals, and the like.

As evident from the equation representing Reaction (II), for every mole of alkyl nitrite consumed, a mole of nitric oxide is generated. Nitric oxide thus formed may be recycled and used as a starting material for forming alkyl nitrites according to Reaction (I), thus completing the nitrite-oxalate reaction cycle. Dialkyl oxalate produced in the carbonylation reaction zone can be purified and recovered as product or further reacted, for example, by contacting it with hydrogen in a hydrogenation reaction zone to produce ethylene glycol.

Unless means are provided for removing various gaseous impurities from the nitrite-oxalate reaction cycle, however, the impurities gradually will increase in concentration in the recycle stream. These impurities include such gases as nitrogen, methane and carbon dioxide. One procedure commonly employed to curtail or counteract the buildup of inert impurities in a cycle is to withdraw or purge a small portion of a recirculating stream in the cycle and dispose of that portion, for example, to the atmosphere.

However, a purge stream taken from a nitrite-oxalate reaction cycle in accordance with the present invention will contain nitric oxide and alkyl nitrite in amounts which could have a harmful environmental effect. Nitric oxide is present as a result of using a molar excess thereof in the production of alkyl nitrite. In addition to potentially harmful effects on the environment, the loss of nitric oxide and alkyl nitrite by purging would represent a significant loss of valuable materials. Accordingly, nitric oxide and alkyl nitrite must be removed from any purge stream prior to discharging the impurities to the atmosphere.

A further consideration is that the approach taken should not result in formation of adverse amounts of materials deleterious to the integrated process. That is, in attempting to solve the problem presented by the need to purge impurities from a recirculation stream, which impurities are in admixture with otherwise valuable materials which themselves are potentially harmful to the atmosphere, it also is necessary to avoid forming and introducing materials into the integrated process which (1) adversely affect the formation of alkyl nitrite or dialkyl oxalate, and (2) reduce the economics of the process by requiring their subsequent separation from desired products. The present invention, then, is directed to a process for purging gaseous impurities from an integrated process while alleviating or avoiding these problems.

BRIEF DESCRIPTION OF THE DRAWINGS

The drawing is a schematic flow chart of an integrated nitriteoxalate production cycle.

DESCRIPTION OF THE INVENTION

In accordance with the present invention, a process is provided for removing impurities from the gaseous product stream of an alkyl nitrite production zone. The process comprises:

(a) contacting at least a portion of the gaseous product stream containing nitric oxide, alkyl nitrite and impurities recovered from an alkyl nitrite production zone, a lower alcohol and oxygen in a reaction zone to produce a recovery stream substantially free of nitric oxide, the oxygen being present in the reaction zone in an amount such that the mole ratio of nitric oxide to oxygen is in the range of from about 4:1 to about 2:1 and the lower alcohol being present in the reaction zone in an amount such that the mole ratio of nitric oxide to lower alcohol is about 1:1 or less;

(b) withdrawing said recovery stream from the reaction zone, the recovery stream containing alkyl nitrite and impurities and being substantially free of nitric oxide;

(c) removing at least a portion of the alkyl nitrite from the recovery stream; and (d) purging at least a portion of the recovery stream from which the alkyl nitrite has been removed.

The process in accordance with this invention has particular application in an integrated alkyl nitrite-dialkyl oxalate production cycle.

The subject invention will be more easily understood with reference to the drawing. Alkyl nitrite is produced in an alkyl nitrite reactor or alkyl nitrite regeneration column 10 (ANRC) by contacting nitric oxide and oxygen in the presence of a lower alcohol. In terms of the present invention, the lower alcohol includes $C_1$ to $C_4$ alcohols and preferably is selected from methanol, ethanol and mixtures thereof. Methanol is most preferred and thus the present invention will be described using methanol as the lower alcohol and methyl nitrite as the product.

Recycle nitric oxide, typically supplemented by makeup nitric oxide (solid line 31 and/or dotted line 32), is fed into the ANRC via line 20. Oxygen is supplied to the ANRC via line 21. The nitric oxide and oxygen streams preferably are supplied to the bottom of the ANRC. Liquid methanol is supplied to the top of the ANRC via line 22. Methanol advantageously serves as both a reactant and a scrubbing agent, as described more fully below.

As discussed above, the mole ratio of nitric oxide to oxygen in the ANRC preferably is greater than 4:1, typically ranging from slightly greater than 4:1 to 5:1. The actual flow rates of the various reactants into the ANRC can vary widely according to the ANRC design and size. The mole ratio of methanol to oxygen typically is in the range of from about 4:1 to about 12:1 or higher.

Methyl nitrite production preferably is carried out in a continuous manner at temperatures sufficiently high to maintain substantially all of the nitrogen oxide and methyl nitrite and only a portion of the lower alcohol (methanol) in the vapor state. The temperature in the ANRC typically is in the range of from about 10° to about 150° C., preferably from about 20° to about 130° C., and most preferably from about 30° to about 110° C.

The pressure within the ANRC is typically in the range of from about atmospheric to about 100 psia, preferably from about 20 to about 60 psia. Subatmospheric pressures, i.e., pressures less than 14.7 psia may be employed, if desired.

The gas hourly space velocity in the ANRC generally ranges from about 120 to about 36,000 $hr^{-}$, preferably from about 1800 to about 36,000 $hr^{-1}$. Smaller or larger space velocities may be employed depending on the temperature, pressure reactant molar ratios, gaseous diluent, and feed rate employed, so long as sufficient time for reaction is provided. In addition, the reactor design and geometry may have an effect on the preferred space velocity.

In general, the methyl nitrite formation process does not require the use of a catalyst. However, if desired, a suitable catalyst and/or catalyst support may be employed.

Mixing of the various feedstreams supplied to the reaction zone generally is achieved through the turbulent conditions present at their points of introduction, although mixing may be induced by other means as well.

Particularly preferred designs for the ANRC are disclosed in copending application, U.S. Ser. No. 102,367, filed contemporaneously herewith in the name of J. R. Nelson, entitled "Process and Reaction Vessel for Production of Alkyl Nitrite", which is incorporated herein by reference.

The reactants supplied to the ANRC preferably are reacted according to Reaction(I):

$$2NO + \tfrac{1}{2}O_2 + 2ROH \rightarrow 2RONO + H_2O \qquad \text{I}$$

wherein R is methyl.

Unfortunately, some nitric oxide also is converted to nitric acid via the side reactions previously described. Thus, the material leaving the ANRC typically comprises nitric oxide, carbon monoxide, oxygen, and methyl nitrite together with a small amount of nitric acid, water and methanol. Substantially all of the nitric oxide, unreacted oxygen and methyl nitrite product exiting the ANRC are withdrawn from the top of the ANRC in the gaseous phase via line 23.

As mentioned above, a portion of the methanol supplied to the ANRC comprises a reactant, while a portion of it remains in the liquid phase as a scrubbing agent to scrub substantially all of nitric acid and water in the ANRC. Thus, substantially all of the nitric acid and water exiting the ANRC is removed in a liquid methanol-containing stream 24 which preferably is withdrawn from the bottom of the ANRC. Any water that does not exit the ANRC via the methanol-containing stream 24 is withdrawn from the top of the ANRC in the gaseous phase via line 23. A small portion of the methanol exiting the ANRC also is withdrawn from the top of the ANRC in the gaseous phase via line 23.

The liquid stream withdrawn from the ANRC via line 24 may be refined by distillation, extraction or the like to reduce its water and nitric acid content. The refined product then may be recycled as the lower alcohol.

In the integrated, alkyl nitrite-dialkyl oxalate process depicted in FIG. 1, at least a portion of the overhead vapor stream 23 from the ANRC, generally the major portion, is mixed with carbon monoxide supplied via line 26, preferably in the gaseous phase, and is supplied to a carbonylation reaction zone or oxalate reactor 11. Preferably all the materials entering oxalate reactor are substantially completely in the gaseous phase. In reactor 11, methyl nitrite is contacted with carbon monoxide in the presence of a catalyst to form dimethyl oxalate and nitric oxide according to Reaction (II):

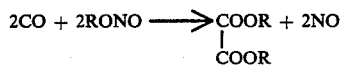
$$2CO + 2RONO \longrightarrow \underset{COOR}{COOR} + 2NO \qquad (II)$$

wherein R is methyl.

It may be preferable to carry out the carbonylation reaction in the presence of an inert gaseous diluent such as nitrogen or carbon dioxide. Carbon dioxide is preferred since it provides a higher heat capacity in comparison with nitrogen. Such gaseous diluent may comprise from about 0 to about 99 percent by volume of the gaseous feed. Typically, the concentration of gaseous diluent ranges from about 1 to about 90 percent by volume.

Suitable concentrations of carbon monoxide in the reaction mixture depend on the alkyl nitrite employed and its concentration, the catalyst used, the concentration of inert gaseous diluent, if diluent is employed, and the selected process conditions. In general, the higher the concentration of the alkyl nitrite, the more rapid the carbonylation reaction. The ratio of alkyl nitrite to carbon monoxide, by volume, typically is in the range of from about 0.05 to about 3.0, preferably from about 0.2 to about 1.0. A molar excess of carbon monoxide normally will be used.

The carbonylation reaction is carried out under conditions which essentially avoid the formation of a liquid phase in the carbonylation reaction zone 11. These conditions may vary depending upon the particular alkyl nitrite and its concentration. The carbonylation reaction generally is carried out at a temperature of from about 50° to about 200° C., preferably from about 75° to about 160° C., most preferably from about 120° to about 150° C. The carbonylation reaction pressure generally is from about atmospheric to about 220 psia, more preferably from about atmospheric to about 100 psia, and most preferably from about 15 psia to about 60 psia. Subatmospheric pressure may be employed, if desired. The gas hourly space velocity for the carbonylation reactor generally is greater than about 120 hr$^{-1}$, preferably from about 360 hr$^{-1}$ to about 72,000 hr$^{-1}$.

The carbonylation reaction zone 11 preferably does not contain water. While a very minor amount of water may be tolerated in the reaction zone, preferably substantially all of the water formed in the ANRC is removed prior to introducing the ANRC product stream into carbonylation reaction zone 11. The amount of water in the oxalate-forming reaction zone preferably is less than about 0.5 percent by volume.

The carbonylation reaction preferably is carried out in a continuous manner in a series of elongated tubular zones although alternative zone geometries and designs may be employed. The materials of construction should be such that they are inert to the reactants and products and are able to withstand reaction temperatures and pressures. Due to the exothermic nature of the carbonylation reaction, carbonylation reaction zone 11 may be fitted with internal or external heat exchange unit(s) to control temperature. Mixing in carbonylation reaction zone 11 generally is achieved through turbulence at the points of introduction for the various gaseous components. Other mixing mechanisms may be employed as well.

Carbonylation reaction zone 11 preferably is packed with a solid catalyst of the platinum group metal series. The preferred platinum group catalyst material is palladium. However, platinum, rhodium, ruthenium, and iridium also are useful. Furthermore, salts of these metals such as nitrates, sulfates, phosphates, halides, acetates, oxalates, or benzoates may be used. These materials may be supported on a carrier such as active carbon, alumina, silica, silica-alumina, diatomaceous earth, pumice, magnesia, or zeolite. The amount of platinum group metal generally ranges from about 0.01 to about 10 percent by weight, preferably from about 0.2 to about 2 percent by weight, relative to the carrier. The solid catalyst generally may be supplied as a fixed bed or as a fluidized bed.

When a palladium catalyst is employed, it has been found that nitrous and nitric acids tend to accelerate the rate of deactivation of the catalyst. It is therefore preferable that substantially all of the nitrous acid produced in or supplied to the ANRC be consumed in the ANRC. Furthermore, since oxygen has similar deleterious effects on such catalysts, it is important to minimize the amount of unconsumed oxygen in the alkyl nitrite product recovered from the ANRC.

Carbonylation reaction effluent 28, comprising dimethyl oxalate and nitric oxide is withdrawn from the carbonylation reaction zone 11 substantially completely in the vapor phase and preferably is supplied to an oxalate scrubber 12. A liquid scrubbing agent supplied to oxalate scrubber 12 via line 29 scrubs substantially all of the dimethyl oxalate from the carbonylation reaction effluent. Preferably, the scrubbing agent is the same material used as a scrubbing agent in the ANRC, i.e., methanol. A liquid bottoms stream 30 comprising the scrubbing agent and dimethyl oxalate, is withdrawn from the bottom of oxalate scrubber 12. Substantially all of the nitric oxide contained in the carbonylation reaction effluent 28, i.e., 95 percent or more, preferably 99 percent or more, is withdrawn from oxalate scrubber 12 in a gaseous overhead stream 20 and preferably is recycled to the ANRC, thereby completing the nitrite-oxalate cycle. Since some nitric oxide is consumed via side reactions in the ANRC, e.g., via the production of unwanted nitric acid, nitric oxide recovered from oxalate scrubber typically must be supplemented by makeup nitric oxide fed to the ANRC as a separate stream via line 31 or introduced into the recycle nitric oxide stream 20 via dotted line 32.

The gaseous nitrite-oxalate reaction cycle thus involves the following sequence:

(1) a gaseous ANRC product stream is withdrawn from the ANRC and is contacted with gaseous carbon monoxide supplied via line 26 in carbonylation reaction zone 11;

(2) a gaseous carbonylation reaction zone product stream is withdrawn from carbonylation reaction zone via line 28 and is sent to oxalate scrubber 12;

(3) a gaseous oxalate scrubber stream is withdrawn from oxalate scrubber 12 via line 20, is combined with makeup nitric oxide supplied via line 31 and is contacted in the ANRC with gaseous oxygen supplied via line 21 and with a lower alcohol such as methanol or ethanol supplied via line 22.

In accordance with the present invention, an impurities removal stream or purge stream 40 is removed from the recirculating flow in the nitrite-oxalate reaction cycle in a sufficient amount to prevent the continuous buildup of impurities, impurities being defined as (1) components introduced via the reactants, such as nitrogen in the nitric oxide makeup feedstream 31 and methane in carbon monoxide feedstream 26, and (2) by-products, such as carbon dioxide, produced in the carbonylation reaction zone 11. The impurities removal stream 40 comprises a minor portion of the gaseous ANRC product stream 23, typically less than about 10 percent of the gaseous ANRC product stream 23, preferably less than about 4 percent, and most preferably about 1 percent of the ANRC gaseous product stream 23. Impurities removal stream 40 contains, in addition to impurities such as nitrogen, methane and carbon dioxide, significant amounts of methyl nitrite produced in the ANRC as well as unreacted nitric oxide.

As discussed above, nitric oxide and methyl nitrite are useful materials for producing dialkyl oxalates. To simply discard such materials represents a loss of substantial amounts of valuable materials. Furthermore, releasing these amounts of nitric oxide and methyl nitrite to the atmosphere may be harmful to the environment. Thus, for both economical, as well as ecological reasons, the present invention provides a method for recovering at least a portion of the nitric oxide and methyl nitrite contained in impurities removal stream 40.

In accordance with these objectives, a blow-off nitrite reactor 13 is provided for converting substantially all of the nitric oxide in impurities removal stream 40 to alkyl (methyl) nitrite. The impurities removal stream 40 is supplied to the blow-off reactor in the vapor phase.

Blow-off reactor 13 functions in a manner generally similar to the ANRC in that nitric oxide is oxidized in the presence of a lower alcohol such as methanol to form methyl nitrite and water. Some by-product nitric acid also is formed. Methanol is introduced as a liquid to the top of the blow-off reactor via line 33 and serves both as a reactant for converting $N_2O_3$ to alkyl nitrite as well as a scrubbing agent for scrubbing water and nitric acid by-products formed in reactor 13.

Blow-off reactor 13 differs from the ANRC in that sufficient oxygen is provided via line 34 to consume substantially all of the nitric oxide supplied to the blow-off reactor 13. In other words, a molar excess of oxygen relative to nitric oxide, in accordance with the stoichiometry of Reaction (I), is fed to reactor 13. By "substantially all" is meant at least 95 percent and preferably 99 percent or more of the nitric oxide is consumed. In this way, a recovery stream containing methyl nitrite but substantially free of nitric oxide, is produced. A high nitric oxide conversion, i.e., at least 95 percent, of that fed is necessary to remove the nitric oxide from the purge stream prior to venting it to the atmosphere.

It also is desired that a high conversion be accomplished without the formation of excessive amounts of other unwanted by-products, such as nitric acid, methylal, methyl formate, methyl nitrate or the like, methylal and methyl formate being undesirable in part because of the difficulty in purging them from the system. Previous work had raised a concern that such undesirable by-products would be formed in unacceptable amounts. Importantly, the process in accordance with this invention provided the desired high conversion of nitric oxide in reactor 13 without the formation of excessive amounts of these undesirable by-products. Of the nitric oxide converted, 95 percent or more, indeed as much as 99 percent or more, is converted to the desired methyl nitrite.

Oxygen stream 34 and the impurities removal stream 40 are fed to the bottom of the blow-off reactor 13 in the gaseous phase, while the lower alcohol stream 33, e.g., methanol or ethanol, is supplied as a liquid to the top. As noted above, oxygen provided via line 34 is present in at least a stoichiometric amount relative to nitric oxide, and preferably is present in excess of stoichiometry. However, too large an excess of oxygen is undesirable because it contributes to the formation of undesirable by-products, e.g., $N_2O_4$, which in turn leads to the formation of nitric acid. Accordingly, the desired mole ratio of nitric oxide to oxygen in blow-off reactor 13 is within the range of from about 4:1 to about 2:1.

Tails stream 35 withdrawn from the blow-off reactor 13 contains the lower alcohol, i.e., methanol, in addition to some water and nitric acid. Methanol in stream 35 preferably is recovered by any suitable means. Depending on the concentration of stream 35, the tails stream 35 may be introduced directly into the ANRC 10.

The size of blow-off reactor 13 is selected so as to provide adequate volume for the desired impurities removal stream flow rate. Lower alcohol, i.e., methanol, is supplied via line 33 in an amount such that at least a stoichiometric amount called for by Reaction (I), preferably a molar excess of methanol, is present relative to the nitric oxide in the reactor 13, i.e., the ratio of nitric oxide to alcohol is 1:1 or less.

Operating conditions within blow-off reactor 13 are substantially similar to those employed within the ANRC, i.e., conditions of temperature and pressure are maintained such that reaction of oxygen, nitric oxide and methanol in accordance with Reaction (I) as set forth above is encouraged. The design of blow-off reactor 13 is preferably substantially similar to that of the ANRC except that, in general, the blow-off reactor 13 is significantly smaller than the ANRC.

Gaseous blow-off reactor effluent stream 36, comprising methyl nitrite, removed from the top of the blow-off reactor 13 is supplied to blow-off scrubber 14. A liquid scrubbing agent, preferably methanol, is supplied to blow-off scrubber 14 via line 37 to scrub substantially all of the methyl nitrite from gaseous effluent stream 36 supplied to blow-off scrubber 14. Due to the volatility of methyl nitrite, the amount of methanol which is supplied to the blow-off scrubber via line 37 in order to remove substantially all the methyl nitrite is typically much larger than the amount supplied to blow-off reactor 13, for example, an amount of up to about 50 or more times larger.

A liquid tails stream containing the scrubbing agent together with methyl nitrite is removed from the bottom of blow-off scrubber 14 via line 38. This liquid tails stream 38 typically is substantially free of nitric acid and water and can be supplied to the ANRC 10 as at least a portion of the methanol reactant. A gaseous overhead stream 39 substantially free of methyl nitrite and nitric oxide is withdrawn from the top of the blow-off scrubber 14. This gaseous stream simply can be discarded, preferably by venting to the atmosphere. Materials in gaseous stream 39 withdrawn from the top of the blow-off scrubber thus are removed from the nitriteoxalate reaction cycle.

By the process of this invention, impurities which otherwise would accumulate in the recirculating streams of an integrated alkyl nitrite-alkyl oxalate production cycle can be purged, thus preventing their buildup in the system, while avoiding the potentially harmful effects that purging to the atmosphere of the nitric oxide and alkyl nitrite which occur in admixture with such impurities. At the same time, the alkyl nitrite in the purge stream is recovered and used.

Although certain embodiments of the invention have been described in detail, it will be appreciated that other embodiments are contemplated along with modifications of the disclosed features, as being within the scope of the invention, which is defined in the appended claims.

We claim:

1. A process for removing impurities from the gaseous product stream of an alkyl nitrite production zone comprising:
   (a) contacting at least a portion of the gaseous product stream containing nitric oxide, alkyl nitrite and impurities recovered from an alkyl nitrite production zone, a lower alcohol and oxygen in a reaction zone to produce a recovery stream substantially free of nitric oxide, said oxygen being present in said reaction zone in an amount such that the mole ratio of nitric oxide to oxygen in said reaction zone is in the range of from about 4:1 to about 2:1 and said lower alcohol being present in said reaction zone in an amount such that the mole ratio of nitric oxide to lower alcohol is about 1:1 or less;
   (b) withdrawing said recovery stream from said reaction zone, said recovery stream containing alkyl nitrite and impurities and being substantially free of nitric oxide;
   (c) removing at least a portion of the alkyl nitrite from said recovery stream; and
   (d) purging at least a portion of said recovery stream from which the alkyl nitrite has been removed.

2. The process of claim 1 wherein said alkyl nitrite is methyl nitrite and said lower alcohol is methanol.

3. The process of claim 2 wherein the nitric oxide content in said recovery stream is one percent or less.

4. The process of claim 3 wherein of the nitric oxide contacted, 95 percent or more is converted to methyl nitrite.

5. The process of claim 4 wherein of the nitric oxide contacted, 99 percent or more is converted to methyl nitrite.

6. The process of claim 2 wherein a bottoms stream is withdrawn from said reaction zone, said bottoms stream comprising methanol, methyl nitrite and water.

7. The process of claim 1 wherein alkyl nitrite removed in step (c) is recycled to said alkyl nitrite production zone.

8. The process of claim 1 wherein said portion of the gaseous product stream is a sufficient amount to prevent the buildup of impurities.

9. The process of claim 8 wherein said portion is less than about 10 percent of the gaseous product stream.

10. The process of claim 9 wherein said portion is less than about 4 percent of the gaseous product stream.

11. The process of claim 10 wherein said portion is about 1 percent of the gaseous product stream.

12. The process of claim 1 wherein said process is carried out in a continuous manner.

13. The process of claim 1 wherein said alkyl nitrite is ethyl nitrite and said lower alcohol is ethanol.

14. A process for removing impurities from the effluent of an alkyl nitrite production zone comprising:
   (a) contacting at least a portion of the gaseous product stream containing nitric oxide, alkyl nitrite and impurities recovered from an alkyl nitrite production zone, a lower alcohol and oxygen in a reaction zone to produce a recovery stream substantially free of nitric oxide, said oxygen being present in said reaction zone in an amount such that the mole ratio of nitric oxide to oxygen in said reaction zone is in the range of from about 4:1 to about 2:1 and said lower alcohol being present in said reaction zone in an amount such that the mole ratio of nitric oxide to lower alcohol is about 1:1 or less;
   (b) withdrawing said recovery stream from said reaction zone, said recovery stream containing alkyl nitrite and impurities and being substantially free of nitric oxide;
   (c) supplying said recovery stream to a scrubbing means;
   (d) supplying liquid scrubbing agent to said scrubbing means;
   (e) withdrawing a bottoms stream from said scrubbing means comprising at least a portion of the alkyl nitrite supplied to said scrubbing means together with said scrubbing agent; and
   (f) withdrawing an overhead stream from said scrubbing means.

15. The process of claim 14 wherein said liquid scrubbing agent comprises methanol.

16. The process of claim 14 wherein said overhead stream is discharged to the atmosphere.

17. The process of claim 14 wherein said bottoms stream is recycled to said alkyl nitrite production zone.

18. The process of claim 14 wherein said alkyl nitrite is methyl nitrite and said lower alcohol is methanol.

19. The process of claim 18 wherein the nitric oxide content in said recovery stream is one percent or less.

20. The process of claim 18 wherein of the nitric oxide contacted, 95 percent or more is converted to methyl nitrite.

21. The process of claim 18 wherein of the nitric oxide contacted, 99 percent or more is converted to methyl nitrite.

22. The process of claim 14 wherein said process is carried out in a continuous manner.

23. A process for removing impurities from a production cycle comprising one or more reactions steps, wherein one of the reaction steps is the production of alkyl nitrite by contacting nitric oxide, oxygen and lower alcohol, comprising:
   (a) contacting at least a portion of the gaseous product stream containing nitric oxide, alkyl nitrite and impurities recovered from an alkyl nitrite production zone, a lower alcohol and oxygen in a reaction zone to produce a recovery stream substantially free of nitric oxide, said oxygen being present in said reaction zone in an amount such that the mole ratio of nitric oxide to oxygen in said reaction zone is in the range of from about 4:1 to about 2:1 and said lower alcohol being present in said reaction zone in an amount such that the mole ratio of nitric oxide to lower alcohol is about 1:1 or less;

(b) withdrawing said recovery stream from said reaction zone, said recovery stream containing alkyl nitrite and impurities and being substantially free of nitric oxide;

(c) removing at least a portion of the alkyl nitrite from said recovery stream; and (d) purging at least a portion of said recovery stream from which the alkyl nitrite has been removed.

24. The process of claim 23 wherein said process is carried out in a continuous manner.

25. The process of claim 23 wherein said alkyl nitrite is methyl nitrite and said lower alcohol is methanol.

* * * * *